United States Patent [19]

Renga et al.

[11] 4,332,729

[45] Jun. 1, 1982

[54] PREPARATION OF CYCLIC CARBONATES

[75] Inventors: James M. Renga; Roy A. Periana-Pillai, both of Midland, Mich.

[73] Assignee: The Dow Chemical Company, Midland, Mich.

[21] Appl. No.: 284,037

[22] Filed: Jul. 17, 1981

[51] Int. Cl.³ .................. C07D 317/38; C07D 317/36; C07D 317/46

[52] U.S. Cl. .................................... 549/229; 549/230

[58] Field of Search ..................................... 260/340.2

[56] References Cited

PUBLICATIONS

Pews, J. Chem. Soc. Chem. Comm., 1974, p. 119.

*Primary Examiner*—Norma S. Milestone
*Attorney, Agent, or Firm*—Douglas N. Deline

[57] ABSTRACT

The thermal decomposition of a halogenated aliphatic carbonate at about 100° C.–300° C. to produce a cyclic carbonate and an aliphatic halide is accelerated by the presence of chemically combined mercury.

8 Claims, No Drawings

PREPARATION OF CYCLIC CARBONATES

BACKGROUND OF THE INVENTION

This invention relates to a new catalytic chemical process for making cyclic alkylene carbonates.

Cyclic carbonates such as ethylene carbonate and propylene carbonate are useful solvents and chemical intermediates. Commonly used processes for making these cyclic esters include the reaction of phosgene with the appropriate glycol and the reaction of a chlorohydrin with carbon dioxide, both carried out in the presence of a base and thus involving the production of a large amount of salt as an undesirable waste by-product.

It is known that β-brominated alkyl carbonates such as 2,3-dibromopropyl ethyl carbonate and 2-bromoethyl ethyl carbonate undergo pyrolysis on long heating at about 200° C. to produce a bromomethylethylene carbonate and ethylene carbonate, respectively, with ethyl bromide as a co-product in each case, see Pews, J.C.S. Chem. Comm., 1974, p. 119. It is also known that these brominated alkyl carbonates and their chlorinated analogs are converted to corresponding alkylene epoxides when they are heated in the presence of a quaternary ammonium or phosphonium salt. This reaction is described in applications of one of us and another, see Renga and Emmons, Ser. No. 095,002, filed Nov. 16, 1979, now U.S. Pat. No. 4,261,906, also Ser. No. 238,188, filed Feb. 25, 1981 entitled Process for Making Vicinal Epoxides and Dihalides, same inventors.

SUMMARY OF THE INVENTION

It has now been found that the decomposition of a β-halogenated alkyl carbonate to form a cyclic alkylene carbonate and an alkyl halide is greatly facilitated and accelerated by the presence of a small but catalytically effective amount of chemically combined mercury. This reaction, which takes place at about 100° C.–300° C., is undergone by halogenated alkyl carbonate esters having the formula $$X-\underset{\underset{R^3}{|}}{\overset{\overset{R^1}{|}}{C}}-\underset{\underset{R^4}{|}}{\overset{\overset{R^2}{|}}{C}}-O-CO_2-A$$

wherein A is an alkyl group, preferably a lower alkyl group, or a group of the formula

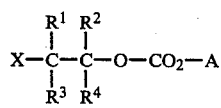

wherein each R group individually is hydrogen, a hydrocarbon group, —CH$_2$X, —CH$_2$Y, and each of the pairs R$^1$, R$^2$ and R$^5$, R$^6$ may together form an alkylene group of 3–6 carbon atoms, each X is individually Cl, Br, or I, and Y is an alkoxy or aroxy group. The products of the reaction are a halide AX and an alkylene carbonate of the formula

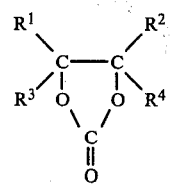

DETAILED DESCRIPTION OF THE INVENTION

In the present mercury-catalyzed reaction, the preferred temperature is about 150° C.–250° C. to provide an optimum combination of conversion and yield with a practical reaction time of about 0.1–10 hours, depending upon the particular halogenated carbonate starting material and especially the halogen in that carbonate ester. Although brominated and iodinated carbonate esters offer faster reaction rates at a given temperature, the chlorinated esters are preferred starting materials in most cases, primarily for economic reasons.

In the above formulas, the term "hydrocarbon group" includes alkyl groups of one to about 20 carbon atoms, cycloalkyl and alkylcycloalkyl groups of 5–10 carbon atoms, and aromatic hydrocarbon groups of 6–10 carbon atoms. Thus, groups such as methyl, ethyl, isopropyl, hexyl, dodecyl, and octadecyl are encompassed by the definition, also groups such as cyclopentyl, cyclohexyl, dimethylcyclohexyl, phenyl, tolyl, and xylyl are included.

The symbol Y defines alkoxy groups, preferably alkoxy groups of 1–4 carbon atoms such as methoxy, ethoxy, isopropoxy, t-butoxy, and the like, and also aroxy groups such as a phenol or bisphenol residue.

In a preferred mode of the present process, the symbol A in the above halogenated carbonate formula represents an alkyl group, most preferably a lower alkyl group such as methyl, ethyl, isopropyl, or butyl. Carbonates where A is methyl or ethyl are advantageous in that the methyl or ethyl halide co-product is most readily vaporized from the reaction mixture, thereby driving the reaction to rapid completion and also facilitating the separation of the relatively high boiling cyclic carbonate product from the residual reaction mixture as a pure material.

When A represents the halogenated group of the formula

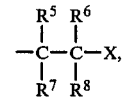

the process is somewhat complicated by the fact that two cyclic carbonates and two alkylene halides are produced, these products having the formulas

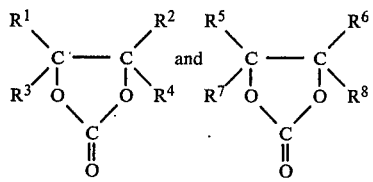

plus

-continued

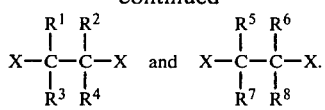

In the case where an unsymmetrical carbonate ester is the starting material and the groups $R^{1-4}$ differ in at least one instance from the groups $R^{5-8}$, the two different cyclic carbonates and the two different alkylene dihalides are ordinarily readily separable by conventional means and, of course, all of the reaction products are commercially valuable compounds as is the case in the mode discussed previously where A represents an alkyl group. Additionally, when an unsymmetrical halogenated carbonate starting material of the above type is employed, the cyclic carbonate product having the higher carbon content is favored. Thus, when $R^{1-4}$ together contain more carbon atoms than $R^{5-8}$, the products

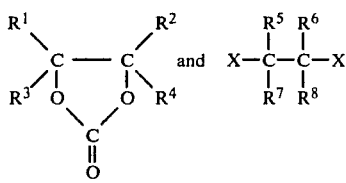

are the major carbonate and dihalide products. Also, a difference in the halogen atoms in the halogenated carbonate starting material affects the course of the reaction. For example, when one X is Cl and the other X is Br in a di(haloalkyl) carbonate, the more labile Br atom favors the formation of the cyclic carbonate derived from the bromoalkyl group.

Obviously, when a symmetrical bis(haloalkyl) carbonate is employed and

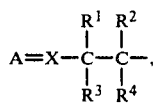

only one cyclic carbonate and one alkylene dihalide are produced.

The β-halogenated alkyl carbonate starting materials for this process can be prepared by several known procedures. The reaction of a chloroformate with an alcohol in the presence of an acid receptor such as pyridine conventionally used for the preparation of carbonate esters is readily adapted to the preparation of these halogenated carbonates by using the appropriate halogenated alcohol and halogenated alkyl chloroformate reactants. Symmetrical bis(haloalkyl) carbonates in particular can be made by the strong acid catalyzed transesterification reaction of a halogenated alcohol in excess with a dialkyl carbonate. Some of these carbonates can also be made by using an appropriate unsaturated alcohol in the transesterification reaction and then adding halogen or hydrogen halide to the unsaturated ester product. Pechukas, U.S. Pat. No. 2,518,058, describes a method for making β-haloalkyl alkyl carbonates by the reaction of an epoxide with a haloformate.

Essentially any mercuric or mercurous compound can be used as the catalyst to accelerate the present reaction. Mercuric salts which are somewhat more soluble in the starting halogenated carbonate are preferred, for example, mercuric chloride, mercuric acetate, mercuric bromide, and mercuric sulfate. The proportion of mercury compound is not critical as any significant amount of mercury has a catalytic effect. In practice, about 0.05–10 mole percent of mercury based on the halogenated alkyl carbonate is a convenient proportion and a preferred range of mercury concentration is about 1–5 mole percent.

The present process is conveniently operated merely by combining the β-halogenated alkyl carbonate ester and the mercury compound catalyst and heating the mixture, whereupon the relatively volatile alkyl halide or alkylene dihalide co-product distills from the reaction mixture and can be recovered by condensing it or by other appropriate means. The cyclic carbonate product is ordinarily distilled from the residual reaction mixture, usually under reduced pressure.

A reaction solvent or diluent is not required and the process is readily operated in the absence of such an inert additive. Inert solvents suitable for use include hydrocarbons such as toluene, xylene, and decane, also glycol diethers such as dimethoxyethane and the diethyl diether of diethylene glycol. It has been found that polar solvents also accelerate the reaction and may be used in place of the mercury catalyst or in combination with it to obtain rapid conversion and good yields. Solvents such as dimethylformamide, N,N-dimethylacetamide, tetramethylene sulfone, and pyrrolidinone are effective for the purpose. A particularly effective and convenient solvent additive to accomplish this result is a cyclic carbonate, preferably the cyclic carbonate product of the process. This variation of the reaction is described and claimed in our companion application Ser. No. 284,036 filed July 17, 1981 concurrently herewith.

EXAMPLE 1

A mixture of 8.32 g (0.05 g mole) of 1-chloro-2-propyl ethyl carbonate and 0.318 g (0.001 g mole) of mercuric acetate was heated to 170° C. in a small reaction flask vented through a receiver cooled to −70° C. After 3 hours, 2.7 g of ethyl chloride had collected in the receiver. Distillation of the residual reaction mixture produced 4.18 g of propylene carbonate, b.p. 59° C.–60° C./0.4 mm Hg, representing 82 percent of the amount theoretically obtainable from the starting carbonate.

EXAMPLE 2

A mixture of 11.14 g (0.05 g mole) of 1-chloro-2-octyl methyl carbonate containing 21 percent of the 2-chloro-1-octyl methyl ester and 0.318 g of mercuric acetate was heated at 200° C. for 2.5 hours in the apparatus of Example 1. Distillation of the reaction mixture remaining after this time produced 7.95 g (92 percent yield) of 4-hexyl-1,3-dioxol-2-one (1,2-octylene carbonate), b.p. 120° C.–121° C./1 mm Hg.

EXAMPLE 3

As shown in the above examples, a mixture of 7.71 g (0.04 g mole) of trans-2-chloro-1-cyclohexyl methyl carbonate and 0.64 g (0.002 g mole) of mercuric acetate was heated at 250° C. for one hour and the residual reaction mixture was distilled to produce 4.55 g (80 percent yield) of cis-1,2-carbonyldioxycyclohexane (1,2-cyclohexylene carbonate), b.p. 95° C.–100° C./0.4 mm Hg.

EXAMPLE 4

In the manner described in the above examples, a mixture of 0.01 g mole of 2,3-dichloro-1-propyl methyl carbonate and 0.0002 g mole of mercuric acetate was heated at 220° C.–225° C. for one hour to produce an isolated yield of 91 percent of the theoretically obtainable (4-chloromethyl)-1,3-dioxol-2-one.

The same product is obtained in essentially the same yield by substituting the isomeric 1,3-dichloro-2-propyl methyl carbonate for the carbonate starting material of Example 4.

EXAMPLES 5–8

A series of experiments was run in which a 2-haloethyl methyl carbonate was heated at 150° C.–155° C. with or without the presence of 2 mole percent mercuric bromide as a catalyst. Effluent methyl halide was trapped in a receiver containing chloroform cooled at −60° C. Conversions and selectivities (to ethylene carbonate) were determined by nuclear magnetic resonance spectroscopic analyses of the liquid in the receiver and the residue in the reaction flask. The data obtained are set forth in Table I.

TABLE I

| Example No. | Halogen | Time Min. | Without Catalyst % Conv. | Without Catalyst % Sel. | with Hg Catalyst % Conv. | with Hg Catalyst % Sel. |
|---|---|---|---|---|---|---|
| 5 | F | 60 | 0 | 0 | 0 | 0 |
| 6 | Cl | 60 | 0 | 0 | 7 | >90 |
| 7 | Br | 9 | — | — | 41 | >95 |
|   |   | 60 | 5 | >95 | 100 | >95 |
| 8 | I | 9 | — | — | 100 | >90 |
|   |   | 60 | 47 | >95 | — | — |

In the above table, values for the selectivity, the percentage of converted haloethyl methyl carbonate going to ethylene carbonate, were estimated since by-products were not fully characterized. No ethylene oxide was found in any of the products.

EXAMPLES 9–12

Another series of reactions was carried out in which 5.6 g (0.03 g mole) of 2,3-dichloro-1-propyl methyl carbonate was heated at 250° C. in the presence of 2 mole percent of a metal salt using a 25 ml reaction flask equipped with a condenser connected to a receiver containing 10 ml of methylene chloride cooled to −70° C. The progress of the reaction was followed to 100 percent conversion in cases where an active catalytic salt was present using gas chromatographic analysis and nuclear magnetic resonance (NMR) analysis of both the liquid in the receiver and the residue remaining in the reaction flask. The results are listed in Table II.

TABLE II

| Example No. | Salt Catalyst | Reaction Time, hr. | % Conv. | % Yield |
|---|---|---|---|---|
| 9 | $HgCl_2$ | 1 | 100 | 90 |
| 10 | $HgBr_2$ | 1 | 100 | 85 |
| 11 | HgCl | 2 | 100 | 87 |
| 12 | $Hg(OAc)_2$ | 1.25 | 100 | 90 |
| A | none | 4 | 100 | 92 |
| B | CuCl | 1.5 | 10 | 95 |
| C | $CuCl_2$ | 1.5 | 12 | 94 |
| D | $Cd(OAc)_2$ | 1.5 | 9 | 93 |
| E | $FeCl_3$ | 1 | 100 | 40 |
| F | $AlCl_3$ | 1 | 100 | 30 |
| G | $SbCl_5$ | 1 | 100 | 30 |

With no added catalyst, the reaction proceeds but has an unduly long initiation period, see Table III. Copper and cadmium salts did not catalyse the reaction. Iron, aluminum, and antimony salts promoted a non-selective reaction.

Some of the experiments of Table II were run over an extended time with periodic analyses of the reaction mixture to determine the degree of conversion of the starting carbonate. These results are listed in Table III.

TABLE III

| Time min. | % Conversion No catalyst | % Conversion $Hg(OAc)_2$ | % Conversion HgCl |
|---|---|---|---|
| 15 | — | 25 | 12 |
| 30 | — | 50 | 35 |
| 45 | — | 80 | 50 |
| 60 | 7 | 95 | 65 |
| 75 | — | 100 | — |
| 90 | — |  | 95 |
| 120 | 25 |  | 100 |
| 150 | 50 |  |  |
| 180 | 90 |  |  |
| 210 | 100 |  |  |

EXAMPLE 13

A 25 ml reaction flask equipped with an adding funnel was connected through a distillation head to a receiver cooled by solid carbon dioxide. After 0.16 g of mercuric acetate was added to the flask, the pressure within the system was reduced to 100 mm Hg and the flask was heated at 180° C. while 6.16 g of 2-chloroethyl 1-bromo-2-propyl carbonate was added portionwise over a 30-minute period. The carbonate was prepared by reacting 1-bromo-2-propanol with 2-chloroethyl chloroformate in the presence of pyridine. Condensed material in the receiver amounted to 2.95 g and was found to be largely a mixture of 1-bromo-2-chloroethane and 1,2-dibromopropane. The residual reaction mixture was distilled to obtain 2.35 g of material collected at 120° C.–125° C. head temperature and 25 mm Hg. NMR and chromatographic analyses of the distillate indicated that 54 percent of the theoretically obtainable amount of propylene carbonate had been formed along with 18 percent of the theoretical yield of ethylene carbonate. The remainder was a mixture of bis(2-chloroethyl) carbonate and 2-chloroethyl 1-chloro-2-propyl carbonate formed by disproportionation reactions.

EXAMPLE 14

Following the procedure of Example 13, 10.05 g of 2-chloroethyl 1-chloro-2-propyl carbonate was heated in the presence of 0.54 g of $HgCl_2$ for 6 hours. The reaction mixture remaining in the flask was distilled as before to produce 4.2 g of distillate containing 35 percent of the theoretically obtainable propylene carbonate and 28 percent of the theoretically obtainable ethylene carbonate. The condensate in the cold trap was essentially a mixture of ethylene dichloride and propylene dichloride.

Following the procedures described in the foregoing examples, other cyclic carbonates are prepared from the appropriate β-halogenated alkyl carbonates. For example, 4-(methoxymethyl)-1,3-dioxol-2-one (methoxymethylethylene carbonate) is produced from 1-chloro-3-methoxy-2-propyl methyl carbonate, 4-(hexyloxymethyl)-1,3-dioxol-2-one is made from 1-chloro-3-hexyloxy-2-propyl ethyl carbonate, and 4-(phenoxymethyl)-1,3-dioxol-2-one is made from bis(1-chloro-3-phenoxy-2-propyl) carbonate.

What is claimed is:

1. A process for making a cyclic alkylene carbonate of the formula

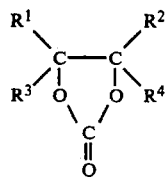

which comprises heating a β-halogenated carbonate ester at about 100° C.–300° C. in the presence of a catalytically effective amount of chemically combined mercury and isolating said cyclic carbonate from the reaction mixture thereby formed, said halogenated carbonate ester having the formula

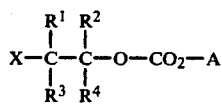

wherein A is an alkyl group or a group of the formula

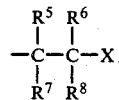

wherein the R groups are individually hydrogen, a hydrocarbon group, —CH$_2$X, —CH$_2$Y, and each of the pairs R$^1$, R$^2$ and R$^5$, R$^6$ may together form an alkylene group of 3–6 carbon atoms, each X is individually Cl, Br, or I, and Y is an alkoxy or aroxy group.

2. The process of claim 1 wherein the temperature is about 150° C.–250° C.

3. The process of claim 1 wherein X represents Cl.

4. The process of claim 1 wherein A represents a lower alkyl group.

5. The process of claim 4 wherein the β-halogenated carbonate ester is 2-chloroethyl methyl carbonate and the cyclic carbonate product is ethylene carbonate.

6. The process of claim 4 wherein the β-halogenated carbonate ester is 1-chloro-2-propyl ethyl carbonate and the cyclic carbonate product is propylene carbonate.

7. The process of claim 4 wherein the β-halogenated carbonate ester is 2,3-dichloro-1-propyl methyl carbonate and the cyclic carbonate product is chloromethylethylene carbonate.

8. The process of claim 1 wherein A represents the group of the formula

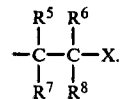

* * * * *